United States Patent [19]

Kabara

[11] 4,189,481

[45] Feb. 19, 1980

[54] ANTIMICROBIAL COMPOSITIONS

[75] Inventor: Jon J. Kabara, Okemos, Mich.

[73] Assignee: Michigan State University, Lansing, Mich.

[21] Appl. No.: 633,036

[22] Filed: Nov. 18, 1975

[51] Int. Cl.² .................. A01N 9/22; A01N 9/20; A01N 9/24
[52] U.S. Cl. .................. 424/248.54; 424/263; 424/267; 424/320; 424/324
[58] Field of Search .......... 424/324, 267, 320, 248.54, 424/263

[56] References Cited

U.S. PATENT DOCUMENTS

| 3,934,029 | 1/1976 | Kabara | 424/320 |
| 3,934,030 | 1/1976 | Kabara | 424/320 |
| 3,934,031 | 1/1976 | Kabara | 424/320 |
| 3,934,035 | 1/1976 | Kabara | 424/320 |

*Primary Examiner*—Frederick E. Waddell

[57] ABSTRACT

A class of aminimides structurally characterizable as dipolar ions wherein a quaternary nitrogen atom is directly bonded to the nitrogen anion of an organic amide having a quaternary nitrogen atom in the acyl residue thereof exhibit broad spectrum inhibitory activity against bacterial and fungal organisms.

6 Claims, No Drawings

ANTIMICROBIAL COMPOSITIONS

BACKGROUND OF THE INVENTION

1. Field of the Invention

This invention relates to a class of nitrogenous compounds as antimicrobial agents for the control of bacterial and fungal growth.

2. Description of the Prior Art

Considerable effort has been directed during the past several decades towards developing antimicrobial agents having a high activity against a broad spectrum of microorganisms including bacteria and fungi, but which at the same time exhibit acceptable tolerable physiological properties. It is generally accepted that hexachlorophene of all of such antimicrobials proposed to date comes about the closest to meeting these desiderata. Unfortunately the use of halogenated compounds of this type has been severely restricted because of the recent unfortunate events stemming from what many feel amounted to a conspicuous misuse of hexachlorophene. Accordingly a present need exists for an effective antimicrobial of this type devoid of the chemical characteristics associated with the indicated halogenated compounds.

It has recently been reported that certain fatty amines and fatty amides evidence antimicrobial activity. Although the activity of these compounds fails to measure up to that demanded for a practical antimicrobial agent, the low order of toxicity attributed to compounds of this type renders these findings highly significant.

SUMMARY OF THE INVENTION

In accordance with the present invention a method is provided for inhibiting the growth of bacteria and fungi which comprises applying to said organisms or their loci an antimicrobially effective amount of a compound of the formula $$\overset{\ominus}{X} \cdot \overset{\oplus}{Y} - CH_2 - \overset{O}{\underset{\|}{C}} - \overset{\ominus}{N} - \overset{\oplus}{N} \overset{CH_3}{\underset{CH_3}{\diagdown}} \overset{OH}{\underset{|}{CH_2 CH(CH_2)_n H}}$$

wherein n is an integer of from 10–16; X is chloro, bromo or iodo; and Y represents a radial selected from the group consisting of benzyldimethylammonium, 2-(hydroxyethyl)dimethylammonium, N-methylpiperidinium, N-methylmorpholinium and pyridinium.

Further related compounds coming within the scope of this invention but whose formuli do not conform to that given above include the following:

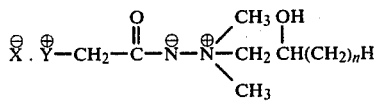

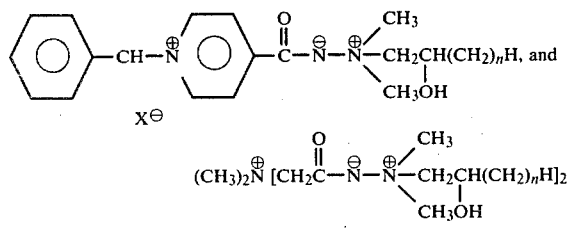

wherein X and n have the same meaning as given above.

The antimicrobial agents of this invention in essentially micro concentrations exhibit surprisingly effective broad spectrum inhibitory activity against bacterial and fungal organisms. Moreover, the dipolar ion configuration of these compounds renders them highly hydrophilic in nature which is an important property in respect of numerous use applications for which the compounds are suited.

DESCRIPTION OF THE PREFERRED EMBODIMENTS

As indicated previously the practice of this invention resides in the use of the antimicrobial agents described above as the active ingredient in a variety of conventional compositions for medicinal, cosmetic or disinfectant purposes. These compositions can be in the form of solutions, as well as solid, liquid or pasty suspensions and emulsions wherein the carrier or vehicle portion is water, oil, or an organic solvent, such as, for example, ethanol. Likewise these compositions can be solid admixtures including the pulverulent form thereof.

Representative of the foregoing compositions include cosmetic oils, salves, cremes, pencils and powders; personal care items such as the spray, stick or powder deodorants, mouthwashes, hair rinses, skin lotions, foot powders and the like; and cleaning compositions such as detergent bars, shampoos and toothpastes. Further, the antimicrobial agents of this invention can be advantageously employed in washing, rinsing, cleaning, disinfecting and preserving compositions for textiles, leather, etc. Still a further important use of these agents can be found in the cleaning and disinfecting compositions designed for use in hospitals and such cleanliness sensitive industrial establishments as dairies, breweries and laundries. The amount of the antimicrobial agent present in the contemplated compositions obviously depends on the particular use for which the overall composition is designed. Generally, in toothpaste, deodorants, cosmetics and foot powders and the like the amount of the antimicrobial agent ranges from about 0.1 to 3.0% based on the total weight of the composition. In applications of a cleansing and disinfecting nature as noted above, the concentration of the agent in these instances can range up to about 10%.

The manner whereby the compounds useful in the practice of this invention can be prepared is well documented in the relevant art and thus need not be exemplified herein. All of the contemplated compounds, except one, can be prepared by a general procedure involving first quaternizing an applicable tertiary amine with an ester of halo acetic acid, preferably chloro methyl or ethyl acetate, to provide the corresponding quaternary ammonium derivative which is then converted to the desired aminimide by reaction with unsymmetrical dimethyl hydrazine and an appropriate long chain terminal epoxide, all as described in detail in U.S. Pat. No. 3,485,806. The applicable tertiary amines for preparing the contemplated compounds as aforesaid include triethylamine, benzyldimethylamine, 2-(hydroxyethyl)-dimethylamine, N-methylpiperidine, N-methylmorpholine, pyridine, and N,N-dimethylglycinate, the latter providing a bisaminimide in accordance with U.S. Pat. No. 3,485,806 when employing equivalent proportions of the dimethyl hydrazine and epoxide. The remaining contemplated compound can be obtained by quaternizing an ester isonicotinic acid with benzylchloride followed by conversion of the ester group of the quaternized product to the aminimide residue via the procedure of the aforesaid patent.

EXAMPLE

For the purpose of illustrating the antimicrobic activity of the aminimides of the present invention, two gram negative bacteria, five gram positive bacteria and two representative fungi were used in a conventional test procedure for determining inhibitory effect. The identification of these test organisms and their source follows:

| Organism | Source |
|---|---|
| *Escherichia coli* | Clinical Isolate |
| *Psendomonas aeruginosa* | ATCC #10145 |
| *Streptococcus faecalis* (grp. D) | Clinical Isolate |
| *Streptococcus pyogenes* | Clinical Isolate |
| *Staphylococcus aureus* | Hospital Infection |
| *Corynebacterium* | ATCC #10700 |
| *Nocardia asteroides* | ATCC #3308 |
| *Saccaharomyces cerevisiae* | Fleishman |
| *Candida albicans* | Michigan State University Plant Pathology Fungi Collection |

In the test procedure observed, representative aminimides were dissolved in water or 95% ethanol to provide standard solutions having a concentration of 1.0 mg of the test compound per ml of the solvent. A further test series was prepared by diluting with sterile Trypticase Soy Broth to concentrations of 100 ug/ml. Compounds more active than at 100 ug/ml were further diluted in a subsequent test or tests.

Following the preparations of the test solutions as noted above, one drop (0.4±0.01 ml.) of an 18-hour broth culture containing $10^9$ to $10^{12}$ organisms per ml. was added to about 10 cc of each starting dilution of the indicated test compounds as well as to a like sample of plain broth serving as a positive control. After innoculation, the test samples are thoroughly mixed and then incubated at 35° C. in a 5% carbon dioxide atmosphere.

After an 18 hour period of incubation, the minimal inhibitory concentration (MIC) of each compound was determined for each test microorganism. The MIC value is defined as the lowest concentration (ug/ml) of the test compound at which no microscopic evidence of growth is observed. In those instances where the MIC exceeded 1000 ug/ml the compound was rated non-inhibitory (NI). Under those circumstances where the test compond itself causes turbidity so that the MIC proved difficult to determine in accordance with the above procedure, a sample (0.015 ml.) of the well-agitated broth or broths in question were innoculated into a Trypticase Soy agar containing 5% defibrinated sheep blood. The test plate wold then be incubated at 35° C. for 18 hours and thereupon examined for growth.

The identification of the representative compounds tested in accordance with the foregoing procedure is set forth as follows:

$$Cl^{\ominus} \cdot Y^{\oplus} - CH_2\overset{O}{\overset{\|}{C}} - \overset{\ominus}{N} - \overset{\oplus}{N} \diagup \overset{CH_3}{\underset{CH_3OH}{\diagdown}} CH_2CH(CH_2)_n H$$

| COMPOUND | Y | n |
|---|---|---|
| A | benzyldimethylammonium | 14 |
| B | " | 10 |
| C | 2-(hydroxyethyl)dimethylammonium | 14 |
| D | N-methylpiperidinium | 14 |
| E | N-methylmorpholinium | 14 |
| F | pyridinium | 14 |
| H | ⟨phenyl⟩—CH₂—N⊕⟨piperidinium⟩ $\overset{O}{\overset{\|}{C}}-\overset{\ominus}{N}-\overset{\oplus}{N}(CH_3)_2CH_2CH(OH)(CH_2)_{14}H$  Cl⁻ | |
| I | $(CH_3)_2\overset{\oplus}{N}[CH_2\overset{O}{\overset{\|}{C}}-\overset{\ominus}{N}-\overset{\oplus}{N}(CH_3)_2CH_2CH(OH)(CH_2)_{14}H]_2$  Cl⁻ | |

The results of tests are given in the following Table I.

TABLE I

| | MICs (μg/ml) | | | | | | | | |
|---|---|---|---|---|---|---|---|---|---|
| compound-- | * | A | B | C | D | E | F | H | I |
| organism | | | | | | | | | |
| *Escherichia coli* | NI | 100 | NI | NI | 1000 | 100 | 100 | NI | NI |
| *Pseudomonas aeruginosa* | 1000 | NI | 1000 | NI | NI | NI | NI | NI | NI |
| *Streptococcus faecalis* (grp. D) | 10 | 10 | 100 | 10 | 10 | 10 | 10 | 100 | 10 |
| *Streptococcus pyrogenes* | 1 | 1 | 10 | 1 | 1 | 1 | 1 | 1 | 10 |
| *Staphylococcus aureus* | 1 | 1 | 100 | 10 | 10 | 10 | 10 | 1000 | 1 |
| *Corynebacterium sp.* | 1 | 1 | 10 | 10 | 1 | 10 | 1 | 10 | 10 |
| *Nocardia asteroides* | 10 | 10 | 100 | 10 | 10 | 10 | 10 | 100 | 10 |
| *Candida albicans* | NI | NI | 100 | NI | 10 | 100 | 10 | 10 | 100 |
| *Saccharomyces cerevisiae* | 10 | 10 | 100 | 10 | 10 | 10 | 10 | 100 | 10 |

*HEXACHLOROPHENE

What is claimed is:

1. A method of inhibiting the growth of bacteria and fungi which comprises applying to said organisms or their loci an antimicrobially effective amount of a compound of the formula

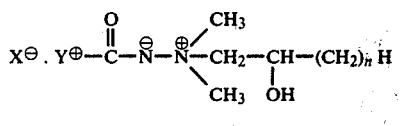

wherein Y represents a quaternary nitrogen residue selected from the group consisting of

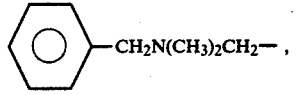

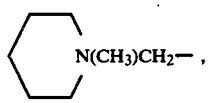

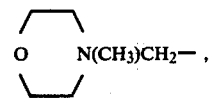

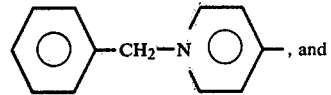

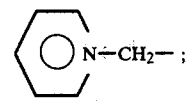

wherein n is an integer of from 10–16; and X is chloro, bromo or iodo.

2. The method of claim 1 wherein X of said formula is chloro.

3. The method of claim 2 wherein n of said formula is 10.

4. The method of claim 2 wherein n of said formula is 12.

5. The method of claim 2 wherein n of said formula is 14.

6. The method of claim 2 wherein n of said formula is 16.

* * * * *